United States Patent [19]

Cuschieri et al.

[11] Patent Number: 5,772,676
[45] Date of Patent: Jun. 30, 1998

[54] ENDOSCOPIC CUTTING DEVICE

[75] Inventors: Alfred Cuschieri; Tim Frank, both of Dundee, Great Britain

[73] Assignee: Karl Storz GmbH & Co., Tuttlingen, Germany

[21] Appl. No.: 532,685

[22] PCT Filed: Feb. 7, 1995

[86] PCT No.: PCT/DE95/00166

§ 371 Date: Feb. 16, 1996

§ 102(e) Date: Feb. 16, 1996

[87] PCT Pub. No.: WO95/20918

PCT Pub. Date: Aug. 10, 1995

[30] Foreign Application Priority Data

Feb. 7, 1994 [DE] Germany ............................ 44 03 602.7

[51] Int. Cl.[6] .................................................. A61B 17/32
[52] U.S. Cl. .............................. 606/167; 606/170; 30/237
[58] Field of Search ................................ 606/1, 110, 113, 606/167, 170, 171, 127, 128; 604/22, 104, 105; 30/237, 253

[56] References Cited

U.S. PATENT DOCUMENTS

| | | |
|---|---|---|
| 3,835,859 | 9/1974 | Keine . |
| 4,590,938 | 5/1986 | Segura et al. ............................ 606/127 |
| 4,733,662 | 3/1988 | Keine . |
| 4,741,335 | 5/1988 | Okada ...................................... 606/127 |
| 5,064,428 | 11/1991 | Cope et al. .............................. 606/127 |
| 5,201,741 | 4/1993 | Keine . |
| 5,509,923 | 4/1996 | Middleman et al. .................... 606/170 |

FOREIGN PATENT DOCUMENTS

| | | |
|---|---|---|
| A569256 | 11/1993 | European Pat. Off. . |
| A2160466 | 6/1972 | Germany . |
| A4204051 | 8/1993 | Germany . |
| A9102493 | 3/1991 | WIPO . |
| A9211816 | 7/1992 | WIPO . |

*Primary Examiner*—William Lewis
*Attorney, Agent, or Firm*—Donald D. Mon

[57] ABSTRACT

Disclosed is an endoscopic cutting device for severing tissue, such as organs, parts of organs or the like, having

- a cutting tool, which is attached at the distal end of said cutting device and which is provided with a cutting blade, and
- an actuating unit which is used to operate said cutting tool and which is attached at the proximal end of said device.

The invented device is distinguished by the cutting blade being disposed approximately parallel to a longitudinal unit which can be varied in length.

8 Claims, 3 Drawing Sheets

FIG. IA
PRIOR ART
FIG. IB
PRIOR ART

ENDOSCOPIC CUTTING DEVICE

TECHNICAL FIELD

The present invention relates to an endoscopic cutting device for severing intracorporal samples, for example, organs or parts of organs, tumors and vessels.

STATE OF THE ART

Accordingly there are numerous suggestions for endoscopic cutting devices:

WO 92/11816 describes a medical cutting instrument, which is provided with a cutting device borne at the distal shaft end thereof in such a manner that it rotates about its longitudinal axis, this cutting device cutting and even cutting up into small pieces propellerlike the to-be-processed corporal samples.

The cutting-up into small pieces procedure occurs in an advantageous manner inside a cover in such a manner that the cut-up small pieces can be easily removed with the cover to the outside through the entry channel.

Disadvantageous is, however, that cut-up small sample pieces are suited to a limited extent for exact histological examination, in particular, as the original form of the severed part of the body has been practically completely lost due to the arbitrary cutting up.

Other cutting devices for severing intracorporal samples are known which are schematically shown in FIGS. 1a and 1b. These are so-called loop cutting devices which are provided at their distal end with wire loops which can vary in the diameter of the loops.

The severance of parts of organs of more stable consistency requires a high cutting force in order to obtain clean cut surfaces. This can be achieved by using as thin as possible cutting wires. However, there is the problem that tear resistency and break resistency of this type of wires is drastically reduced with decreasing wire diameter. In particular, the wires have to undergo quite extreme curvatures when they are drawn together, i.e, during the cutting process. Frequently, in the smallest opening state of the loop, the cutting wires are bent and as a result break at this site.

The object of the present invention is to provide an endoscopic cutting device for severing tissue, such as organs or parts of organs, with which the severance of the to-be-removed and to-be-examined corporal samples and for the cutting up of this sample necessary for the removal of the sample occurs in a controlled manner in such a way that will permit histological examination of the corporal sample as a whole. This means that subsequently all the pieces of the sample can be put back together to form a whole sample.

Moreover, the invented cutting device should be so stable that even samples of relatively strong consistency and firmness can be severed.

BRIEF DESCRIPTION OF THE INVENTION

An element of the present invention is that it is based on an endoscopic cutting device for severing tissue, such as organs, parts of organs or the like, having
- a cutting tool, which is attached at the distal end of the cutting device and which is provided with a cutting blade, and
- an actuating unit which is used to operate the cutting tool and which is attached at the proximal end of the device, and this cutting device is further developed in such a manner that the cutting blade is disposed approximately parallel to a longitudinal unit, the length of which can be varied.

Contrary to the known cutting devices, the invented cutting device is provided with a stationary cutting blade against which the to-be-severed corporal sample is pressed with the aid of the longitudinal unit.

According to a preferred but optional feature of the invention, the longitudinal unit is composed of two elastic bands, which rest in a tautened state along both sides of the cutting blade, which usually is designed straight. The tautened state of the bands can be varied via an actuating unit provided at the proximal end of the instrument.

The elastic bands are firmly fixed at the distal end of the instrument and slide at the other end of the cutting head by means of corresponding guide grooves inside the neck (sometimes called a "support") of the instrument and are finally connected to the actuating unit at the proximal end of the overall instrument.

This arrangement permits, in the untautened state of the elastic bands, forming a bay (sometimes call an "opening"), which is bordered on the one side by the bow-shaped course of the band and on the other side by the straight cutting blade. The to-be-severed corporal sample can be guided through this bay.

By means of visual oberservation during the surgical procedure, the cutting plane can be set at the to-be-severed part of the body in a defined manner and can press the corporal sample against the straight blade in a controlled manner. To do this, the actuating unit at the proximal end of the instrument is operated in such a manner that the parallel running bands are tautened.

Coupled to the process of tautening of the bands, it is particularly advantageous if the cutting blade can be guided in a reciprocably moveable manner in its longitudinal direction. In this way, the simple pressing pressure of the to-be-severed parts of the body against the blade overlaps with the cutting action of the blade which is generated by its back and forth movement in such a manner that the respective part of the body can be more easily severed.

Another embodiment of the present invention also permits reducing the to-be-applied cutting force by the cutting blade against the to-be-severed tissue during tautening of the longitudinal unit In an advantageous manner the bands are designed as rectangular bands composed of a nickel-titanium alloy and usually have a cross section size of 2×0.7 mm.

With the aid of the invented device, under visual observation by means of endoscopes, the cutting surfaces can be placed at the to-be-severed corporal probe in such a manner that it is cut up in a defined way in such a manner that the individual cut up parts of the corporal sample can be put together again for histological examination after having been removed from the corporal cavity. By this means, it is for the first time possible to exactly follow at which sites in the to-be-examined sample, by way of illustration, cancerous cell structures have grown.

BRIEF DESCRIPTION OF THE DRAWINGS

The present invention is made more apparent by way of example in the following without the intention of limiting the scope of the overall inventive concept using preferred embodiments with reference to the drawing, to which moreover reference is explicitly made with regard to all invented details not explained closer herein. The show:

FIGS. 1a, 1b known loop cutting devices,

DETAILED DESCRIPTION OF THE INVENTION

FIGS. 1a and 1b show as such known endoscopic cutting devices, which are provided with a cutting wire 1 which is placed around a to-be-severed corporal sample and tautened respectively tightened with the aid of an actuating element 3 in such a manner that the to-be-separated corporal sample 2 can be severed from the remainder of the part of the body.

FIG. 1a shows a preferred embodiment which is provided with a wire loop disposed laterally at the distal end of the shaft-shaped instrument.

FIG. 1b shows a variant, noteably a so-called wire loop cutting tool at which the cutting wire 1 is disposed as an extension of the shaft-shaped instrument at the distal end thereof.

Figure 2:
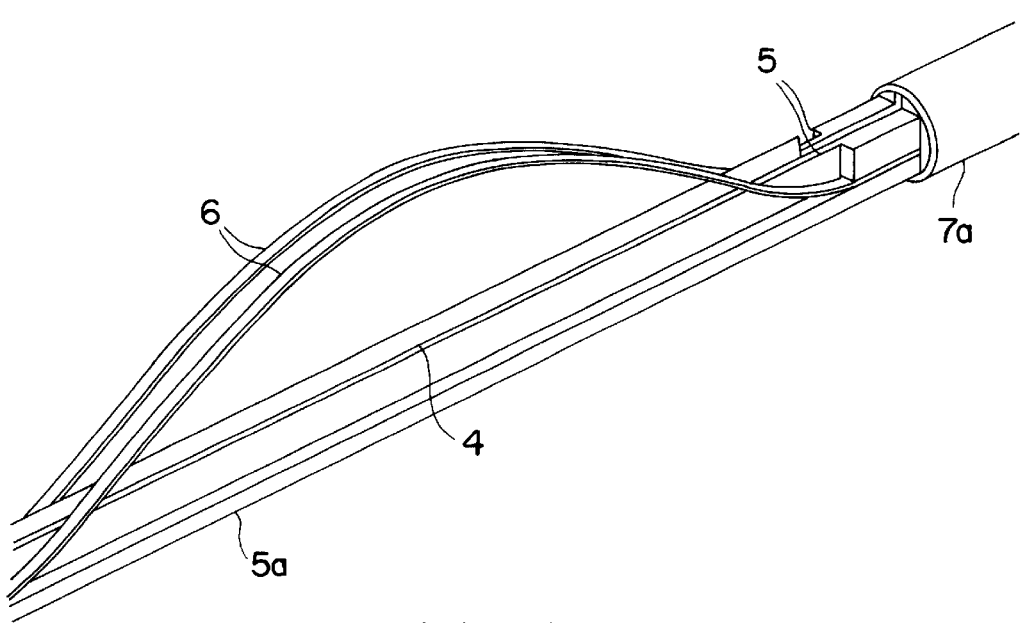
FIG. 2 the distal end of a preferred embodiment of an invented endoscopic cutting device, and FIG. 3 a schematic overall side view of the shown preferred embodiment.

FIG. 2 shows the distal end of a prefered embodiment of an invented endoscopic cutting device according to the invention.

Figure 3:
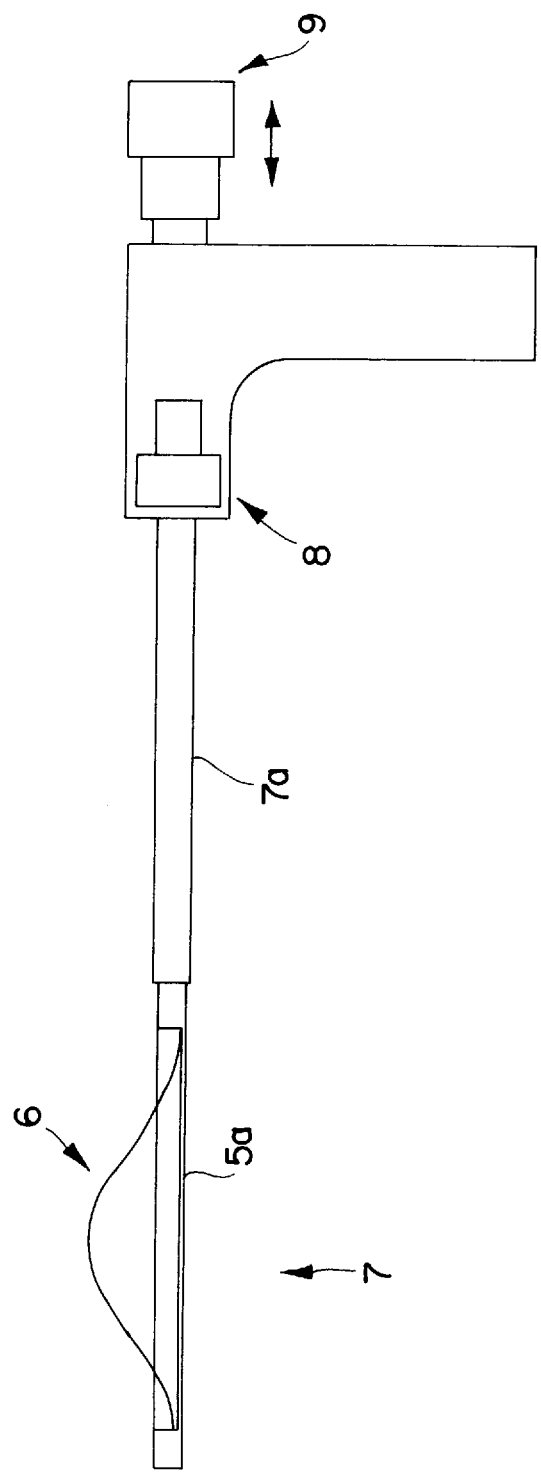

As FIG. 3 shows, the cutting device is attached at the distal end 7 of an instrument provided with a shaft 7a. The elastic bands 6 are as shown in FIG. 2 attached on both sides parallel beside the blade 4 to the distal end of the support 5a and are connected at their opposite ends via actuators 5 to an actuating element 8 (see FIG. 3) in such a manner that the elastic bands 6 can be tautened. In a tautened state, the bands 6 lie below the level of the cutting blade 4, parallel to it close to the housing plates 5. In this way, it is ensured that any material that is inserted between the bands 6 and the cutting blade 4 can be completely severed.

FIG. 3 depicts a schematic side view of the overall cutting instrument. The endoscopic cutting device is attached to the distal end 7. Accommodated in the housing of the instrument is the actuating element 8, with the aid of which the elastic bands 6 are tautened or loosened. During loosening by means of the actuating element 8, the bands assume a preformed, bowlike shape forming a bay (sometimes called an "opening") with the cutting blade. The size of this bay is adaptable to the size of the organ of the to-be-severed corporal samples. The material of which the bands are composed is preferably a nickel-titanium alloy and is provided with a shape-memory effect. Provided at the proximal end of the cutting instrument is an operating unit 9 by means of which the cutting blade can be set into motion. The cutting forces of the cutting blade can be substantially reduced by moving the cutting blade.

What is claimed is:

1. An endoscopic cutting device for severing tissue, said instrument having a longitudinal axis, a proximal end and a distal end, said cutting device comprising:

a support extending axially from said distal end to said proximal end;

a cutting blade mounted to said support, said blade having a cutting edge which extends axially from a location adjacent to said distal end;

an actuator slidably mounted to said support for axial movement parallel to said cutting blade;

a band having a distal end and a proximal end, its distal end being attached to said support adjacent to the distal end of said support, and its proximal end being attached to said actuator, said band being elastic, and in its relaxed shape being formed as an arch, overhanging said cutting blade to form an opening to receive tissue which is to be severed, said band having shape-restoring properties tending to return the band to its arch shape when distortive forces are removed;

whereby, with said band in its relaxed shape, said actuator may be moved toward the proximal end of the instrument, thereby drawing the band and tissue inside said opening toward the support, severing the tissue as it engages the cutting blade, the attachment of the band to the support and to the actuator being closer to the support than the cutting edge of the cutting blade so all of the tissue to be severed is forced past the cutting edge.

2. A cutting device according to claim 1 in which said cutting blade is axially reciprocably mounted to said support, whereby cutting of tissue is facilitated by reciprocation of said cutting blade.

3. A cutting device according to claim 1 in which said band is rectangular in cross-section with one of its dimensions wider than the other, said wider dimension facing said support.

4. A cutting device according to claim 3 in which said band is metallic and springy.

5. A cutting device according to claim 1 in which there is a said band and a said actuator on both sides of said cutting blade, whereby said bands when brought toward said blade by said actuator, straddle the cutting blade.

6. A cutting device according to claim 5 in which said cutting blade is axially reciprocably mounted to said support, whereby cutting is facilitated by reciprocation of said cutting blade.

7. A cutting device according to claim 5 in which said band is rectangular in cross-section with one of its dimensions wider than the other, said wider dimension facing said support.

8. A cutting device according to claim 7 in which said band is metallic and springy.

* * * * *